United States Patent [19]

Ludwig et al.

[11] Patent Number: 5,093,534

[45] Date of Patent: Mar. 3, 1992

[54] PROCESS FOR THE PREPARATION OF SATURATED ALCOHOLS FROM ALDEHYDES

[75] Inventors: Gerhard Ludwig, Haltern; Lothar Fischer; Dieter Hess, both of Marl, all of Fed. Rep. of Germany

[73] Assignee: Huels Aktiengesellschaft, Marl, Fed. Rep. of Germany

[21] Appl. No.: 723,186

[22] Filed: Jun. 28, 1991

[30] Foreign Application Priority Data

Aug. 9, 1990 [DE] Fed. Rep. of Germany ....... 4025245

[51] Int. Cl.$^5$ ................... C07C 29/141; C07C 31/12; C07C 31/125
[52] U.S. Cl. ................................... 568/881
[58] Field of Search .......................... 568/881

[56] References Cited

U.S. PATENT DOCUMENTS

| | | | |
|---|---|---|---|
| 3,431,311 | 3/1969 | Cooper et al. | 568/881 |
| 3,491,158 | 1/1970 | Reich | 568/881 |
| 4,426,541 | 1/1984 | King | 568/881 |
| 4,451,677 | 5/1984 | Bradley et al. | 568/881 |
| 4,626,604 | 12/1986 | Hiles et al. | 568/881 |

FOREIGN PATENT DOCUMENTS

| | | | |
|---|---|---|---|
| 906527 | 9/1962 | United Kingdom | 568/881 |
| 938028 | 9/1963 | United Kingdom | 568/881 |
| 938970 | 10/1963 | United Kingdom | 568/881 |

*Primary Examiner*—J. E. Evans
*Attorney, Agent, or Firm*—Oblon, Spivak, McClelland, Maier & Neustadt

[57] ABSTRACT

A process for the preparation of saturated alcohols from aldehydes is disclosed. The hydrogenation of saturated and unsaturated aldehydes to alcohols can be carried out over catalysts containing cooper and nickel. In the present process, the selectivity of the alcohol preparation is further improved by a combination of an alkaline copper catalyst and a nickel-containing catalyst whose carrier material has acidic centers of a certain acid strength $H_o$.

16 Claims, No Drawings

PROCESS FOR THE PREPARATION OF SATURATED ALCOHOLS FROM ALDEHYDES

BACKGROUND OF THE INVENTION

1. Field of the Invention

The invention relates to a process for the preparation of saturated alcohols by hydrogenating aldehydes in the gas phase in several stages using an alkaline copper catalyst in a first stage and a nickel-containing catalyst in a second stage.

2. Discussion of the Background

It is known that alcohols can be prepared by catalytic hydrogenation of the corresponding saturated and unsaturated aldehydes.

Thus, DE-A-21 50 975 describes the preparation and use of a highly active nickel catalyst on an $SiO_2$ carrier, which contains less than 0.2% of sodium and is also suitable for the hydrogenation of aldehydes. For example, 2-ethylhexanal is hydrogenated using a low hydrogen/aldehyde molar ratio of only 2.5:1 at 36 bar in the liquid phase. The conversion is 96%.

In hydrogenations in the liquid phase, plant pressures of 20 to 300 bar ar usually employed in order to achieve sufficiently complete hydrogenation. Since the reaction is highly exothermic, recycling of a considerable part of the hydrogenated product or dilution with a solvent for capacitive heat removal is necessary in industrial reactors. This permits only relatively low throughputs of aldehydes through the reactors.

These difficulties are avoided by hydrogenation in the gas phase. Thus, in DE-C-1 152 393, gas-phase hydrogenation is carried out in two stages. A copper catalyst is used in the first stage and a copper/nickel catalyst in the second stage. In the gas-phase hydrogenation according to DE-C-1 161 250, a copper catalyst is used in the first stage and a nickel catalyst in the second stage. In both patents, kieselguhr (diatomaceous earth) or kieselguhr modified with sodium phosphate is used as the carrier. The surface of these carriers is neutral or slightly alkaline.

DE-B-1 227 882 describes a two-stage gas-phase hydrogenation over a copper and a palladium catalyst, and a copper/nickel catalyst may also be used in between. Only neutral or slightly alkaline carriers are used here. The copper and nickel contents of the supported catalysts are very high. Furthermore, the products still have considerable residual aldehyde contents.

DE-C-1 276 620 describes a one-stage hydrogenation in the gas-phase over a copper/nickel supported catalyst. However, the comparative example advises against a two-stage hydrogenation over a copper catalyst and then over a copper/nickel catalyst.

According to DE-C-1 276 618, the gas-phase hydrogenation can be carried out in two stages. Here, a copper/nickel catalyst is used in the first stage and a nickel or palladium catalyst in the second stage.

A further improvement in the gas-phase hydrogenation is described in DE-C-1 643 856. Here, the hydrogenation is carried out over silica gel supported catalysts containing copper and/or nickel. The pH of the surface of the silica gel is adjusted to 6–10. The "surface pH" is determined, inter alia, by the method of O. Johnson, J. Phys. Chem. 59, 827 (1955). For aldehydes Which are difficult to hydrogenate and in the case of high space velocity, conventional supported nickel and/or palladium catalysts may also be used downstream. Although no information is given about the surface pH of the downstream catalysts, in this case too the patent suggests a pH of 6 to 10, especially since comparative examples make a distinction with respect to catalysts whose surface pH is less than 6 or greater than 10.

We have found that in this case the formation of hydrocarbons increases sharply and the selectivity decreases substantially at high space velocity.

In DE-A-37 37 277, the hydrogenation, which preferably takes place in two pressure stages, is carried out over a copper/zinc oxide catalyst doped with an alkali metal and/or a transition metal. The catalyst is preferably impregnated with potassium and nickel. According to this patent application, the hydrogenation is improved by the use of an alkaline catalyst.

SUMMARY OF THE INVENTION

Accordingly, one object of the present invention is to improve the yield and selectivity in the gas-phase hydrogenation of saturated and unsaturated aldehydes to saturated alcohols. In particular, it was also intended to prepare, at high space velocities, crude alcohols which meet the high requirements with respect to bromine number and sulfuric acid color index.

This object is achieved by carrying out a multistage hydrogenation according to the following steps.

In a first stage, at least 85% of the hydrogenation reactions are carried out over a particulate, alkaline copper catalyst. In a second stage, a particulate, nickel-containing supported catalyst is used, the carrier having an acidic surface. The surface is characterized in that it contains 0.05 to 0.5 mmol/g of acidic centers which have an acid strength ($H_o$) of 2.8 to 4.8. The catalyst of the second stage is present in particle sizes of 1 to 10 mm diameter, these limits indicating that more than 90% by weight of the catalyst must be in this range. The catalyst of the second stage preferably has particle sizes of 2 to 7 mm.

DETAILED DESCRIPTION OF THE PREFERRED EMBODIMENTS

For the purposes of the present invention, particulate catalysts are, for example, extrudates, pellets, rings, spheres or irregular granules.

The copper catalyst of the first reaction stage can be prepared by conventional methods, as a precipitated or impregnated catalyst. It advantageously contains conventional promoters, such as, for example, chromium oxide, manganese oxide, molybdenum oxide, or phosphate, individually or as a mixture, and 0.5 to 7% of alkali. The copper content may be between about 3 and 80%. An impregnated catalyst containing 5 to 15% of copper is preferably chosen. Suitable carrier materials are oxides of silicon, aluminum, titanium or zinc or mixtures thereof. It is important that the surface of this catalyst has no free acidic centers.

The reaction preferably takes place to a degree of 90–98% over this first catalyst. This relates to the sum of all double bonds capable of undergoing hydrogenation.

The conversion of the first stage is determined by the parameters inlet temperature, concentration of the aldehyde, $H_2$ partial pressure, linear velocity of the reaction components and method and effectiveness of heat removal. The complex reaction makes it impossible to predict the necessary conditions for achieving the desired conversion. The conversion is therefore empirically determined. Thus, for example, the intended amount of copper catalyst can be introduced alone into a test reactor and the variable reaction parameters altered until the desired conversion is achieved. The parameters thus found are scaled up to the industrial reactor.

In another method, a sampling port is mounted in the wall of the reactor, at the boundary between the copper catalyst and the downstream catalyst, and on the basis of the product composition determined at this point, the variable parameters are adjusted so that the conversion according to the invention is achieved in the first stage.

After calibration by one of the above-mentioned methods, measurement of the temperature variation in the reactor is generally a sufficiently precise monitoring and control instrument.

The nickel-containing catalyst of the second reaction stage is preferably a pure nickel catalyst or a copper/nickel catalyst in which the weight ratio of copper to nickel is in the range from 5:1 to 1:5.

The nickel-containing catalyst can be prepared, for example, by precipitation or by pelletizing pulverulent catalyst material. Very good catalysts are obtained if the particulate carrier material is treated with a metal salt solution and then dried. The active material can be applied predominantly in the edge zone. Such catalysts impregnated in the edge zone are preferably used.

The total metal content of the catalyst of the second stage is not a critical parameter. It may be about 3 to 30%. In the case of a catalyst impregnated in the edge zone, the metal content is generally 10 to 20%.

The proportion of the catalyst of the second stage of the total catalyst volume is preferably 20 to 70%, contents of 25 to 45% being particularly preferred.

The nickel-containing catalyst generally contains conventional promoters, such as, for example, chromium oxide, manganese oxide, molybdenum oxide or phosphate, in a total amount of up to 3%, based on the supported catalyst. Contents of 0.3 to 2% ar preferred.

The carrier material preferably consists of alumina or silica, particulate silica gel having a relatively large specific surface area being particularly preferred.

The carrier material preferably has a specific surface area according to Brunauer-Emmett-Teller (BET method) of 100 to 600 m²/g, specific surface areas of 150 to 400 m²/g being very particularly preferred.

A carrier material which has 0.1 to 0.4 mmol/g of acidic centers is preferably used for the second reaction stage. This condition is generally fulfilled by alumina and silica which has been thoroughly washed with acids and water and has a sodium content of up to 0.3%.

The definition of a surface pH according to O. Johnson is problematic since it is scarcely possible to speak of hydrogen ion concentrations in the case of surfaces. We therefore use the definitions and measurement methods of H. A. Benesi, J. Phys. Chem. 61, 970 (1957) in order to characterize the "number and strength" of the acidic centers of the carrier materials.

The acid strengths $H_o$, are assigned color indicators having certain $pK_a$ values. Methyl red having a $pK_a$ value of 4.8 marks one limit. At even higher $pK_a$ values, the acid strength $H_o$ is insufficient. The color indicator 4-aminoazobenzene having a $pK_a$ of 2.8 characterizes the other limit.

In the case of an acid strength $H_o$ defined in this manner, a surface acidity which corresponds to a so-called surface pH (according to DE-C-1 643 856) of about 4 prevails at 0.05 mmol/g of acidic centers.

The hydrogenation process is carried out in several stages, preferably in two or three stages, and a particulate palladium catalyst may be used in the third stage. Supported catalysts on which 0.05 to 5% of palladium have been deposited are preferably used here. Catalysts impregnated in the edge zone and having a palladium content of 0.3 to 0.8% are very particularly preferred.

The carrier of the palladium catalyst preferably has an acidic surface containing more than 0.05 mmol/g of acidic centers. In this case too, carriers having 0.1 to 0.4 mmol/g of acidic centers are particularly preferred.

The volume of the palladium catalyst is generally 5 to 20%, based on the total catalyst volume, an amount of 8 to 15% being preferred.

The individual stages of the hydrogenation can be carried out in several reactors connected in series. Preferably, however, the catalysts are placed in layers one on top of the other in a single reactor with or without separating trays and with or without intermediate cooling means, in such a way that the reaction mixture first flows through the copper catalyst.

The process can be carried out in a single adiabatic shaft reactor (optionally with intermediate cooling) or in a multitube reactor, for example one cooled by pressurized water.

The aldehydes used may be aliphatic saturated and unsaturated aldehydes having 2 to 12 C atoms. Relatively pure aldehydes or crude aldehydes contaminated by preceding processes may be used. Dilution of the aldehydes, for example with alcohols having the same or a smaller number of C atoms, is also sometimes advantageous.

Examples of suitable aldehydes are acetaldehyde, propionaldehyde, acrolein, butyraldehyde, crotonaldehyde, hexanal, 2-ethylhexanal, 2-ethylhexenal, nonanal or decanal.

For the hydrogenation, the aldehyde is first vaporized. Excess hydrogen is mixed with it. The molar ratio of hydrogen to aldehyde is preferably 100:1 to 3:1. A ratio of 30:1 to 5:1 is particularly preferred.

In adjusting the gas mixtures, it should be ensured that the dew point of the mixtures is lower than the reactor inlet temperature for which a temperature in the range from 125° to 160° C. is preferably chosen.

The dew point also depends on the plant pressure. The hydrogenation can be carried out at atmospheric pressure. However, it is also possible to apply slightly reduced pressure down to 500 mbar or superatmospheric pressure up to 20 bar.

The present process has the following advantages:
The hydrogenation can be carried out in a single reactor. Special structural changes to known hydrogenation reactors are not required.
The space velocity and the partial pressure of the aldehyde can be substantially increased while the quality of the discharged hydrogenation product remains the same.
With the same space velocity as in known processes, the selectivity is increased. The formation of hydrocarbons, ethers and esters is further inhibited.

Other features of the invention will become apparent in the course of the following description of exemplary embodiments which are given for illustration of the invention and are not intended to be limiting thereof. The manner in which the invention can be carried out in practice is described below.

Determination of the Number of Acidic Centers in the Carrier Materials 15 g of carrier material is pulverized and is dried for 12 hours at 250° C. in vacuo. About 1 g of sample is filled into each of 10 previously weighed bottles with a screw closure. The sealed bottles are reweighed. The samples are then each covered with a layer of 10 ml of anhydrous cyclohexane, and 0.05 to 0.5 mmol of n-butylamine is introduced in 0.05 mmol portions by adding corresponding amounts of a 0.05 molar solution of n-butylamine in anhydrous cyclohexane. The tightly sealed bottles are then shaken for 24 hours.

2 ml portions of the suspension are introduced into glass containers with a snap cover, and 2 drops of indicator solution are added. The glass containers are arranged in order of increasing n-butylamine content. After half an hour, the amount of n-butylamine required for neutralizing the acidic centers is determined as the equivalence of the number of acidic centers from the glass container which is the first to show a color change.

Preparation of the Catalysts

Silica gel beads having a diameter of 3 to 5 mm, a pore volume of 0.7 cm$^3$/g and a specific surface area of 300 cm$^2$/g are used as the carrier for catalysts A, B and C. The number of acidic centers is measured as 0.15 mmol/g by the Benesi method, using methyl red as an indicator. The acid strength $H_o$ is $\leq 4.8$. 4-Aminoazobenzene (p$K_a$=2.8) shows no color change.

The alkaline catalyst A is prepared by impregnating the carrier with an ammoniacal chromate-containing copper carbonate solution. 0.30 mol of sodium hydroxide solution per kg of carrier is also added to the impregnation solution, so that the acidic centers are 100% overcompensated. After impregnation, the catalyst is dried.

The catalyst B corresponding to DE 1 643 846 is prepared in the same manner using an impregnation solution containing copper nitrate, nickel nitrate and chromate. It is rendered neutral by adding 0.15 mol of sodium hydroxide solution per kg of carrier.

For the preparation of the catalyst C according to the invention, 72 kg of silica gel beads are impregnated in a rotating drum at about 100° C. with 104 kg of an aqueous solution which contains 9.2% of Cu$^{2+}$, 3.95% of Ni$^{2+}$ and 0.923% of Cr(VI) as chromate and 26.4% of NO$_3^-$. The active components are deposited in an edge zone of 0.2 to 1 mm. The beads laden in this manner are first dried in a stream of air and then calcined at temperatures up to 320° C.

The palladium catalyst D has, as a carrier, extruded alumina having a diameter of 1.6 mm, a pore volume of 0.7 cm$^3$/g and a specific surface area of 230 m$^2$/g. According to the Benesi method, the alumina has 0.25 mmol/g of acidic centers and an acid strength $H_o$ of $\leq 4.8$.

The alumina is impregnated with palladium nitrate while rotating in a drum at about 100° C., 1 liter of a 0.7% strength palladium nitrate solution being used per kg of alumina. The palladium is deposited on the carrier in a 0.01 to 0.1 mm thick edge zone. The laden extrudates are dried in a stream of air at 110° C. and then calcined at temperatures up to 450° C.

TABLE 1

| | | Catalysts | | | | |
|---|---|---|---|---|---|---|
| | Carrier | Cu % | Ni % | Cr$_2$O$_3$ % | Pd % | Number of acidic centers in the carrier mmol/g |
| Catalyst A | SiO$_2$ | 9 | — | 1.4 | — | 0 (alkaline) |
| Catalyst B | SiO$_2$ | 10.4 | 4.6 | 1.4 | — | 0 (neutral) |
| Catalyst C | SiO$_2$ | 10.5 | 4.5 | 1.5 | — | 0.15 (acidic) |
| Catalyst D | Al$_2$O$_3$ | — | — | — | 0.66 | 0.25 (acidic) |

Experimental Apparatus

The experimental reactor consists of a jacketed stainless steel tube thermostated by a forced pressurized-water circulation. The internal diameter of the tube is 67 mm and the length about 6.0 m. For temperature measurement, thermocouples are mounted 50 cm apart in a centrally installed inner tube of 8 mm diameter, so that the free cross-section is 34.9 cm$^2$. The reactor is filled to a height of 5.9 m with catalyst, corresponding to a total catalyst volume of 20.4 l.

A jacket-heated evaporator in which the starting materials are vaporized using hot circulating gas is located upstream of the reactor. The gas is circulated with the aid of a recycled gas compressor.

Downstream of the reactor, the hydrogenated product is cooled to less than 20° C. by a water-cooled condenser and is removed in liquid form.

Sampling ports permit the removal of analytical material upstream and downstream of the reactor and at various heights in the catalyst bed. The gas flows through the reactor from top to bottom.

The jacket temperature of the reactor can be regulated with a fluctuation of ±2° C.

Starting Materials a) 2-Ethylhexenal: A crude product is used from a large-scale aldol condensation, which has been separated off from the condensation liquor by decantation. The 2-ethylhexenal content is about 96%.

b) n-Butyraldehyde: This was a distilled commercial product having a content of 99.4–99.6%.

c) iso-Butyraldehyde: This aldehyde is a distilled commercial product having a content of 99.8%.

Analysis

Bromine number: ASTM D 1159-77
Sulfuric acid color index: International Standard (ISO) 1843/8

In Experiments A and B and 1 and 2, the sulfuric acid color indices were determined for the discharged crude hydrogenation mixture.

Gas chromatographic investigation of the products was carried out in a 12 m capillary of type OV 101 (silicone oil) with a temperature gradient of 50° to 250° C. and a heating rate of 8° C./min. In the investigation of the 2-ethylhexanol, a second, 25 m long capillary column of type CW (Carbowax) with the same heating characteristics was additionally used.

In addition to the alcohol contents, the contents of hydrocarbons having 1 carbon atom fewer, and of saturated aldehydes, and the contents of ethers and esters having twice as many carbon atoms were determined by gas chromatography.

Experiments

The experiments were carried out in the reactor described above, at a hydrogen pressure of 6.0 bar absolute and at a GHSV (gaseous hourly space velocity) of 900 h$^{-1}$ (=900 m$^3$ (S.T.P.) of H$_2$ per m$^3$ of catalyst per hour).

Below, comparative experiments are designated by letters and experiments according to the invention by numbers.

In Comparative Experiment A, the alkaline copper catalyst A was used as the sole catalyst. In Experiments 1 and 2, catalyst A was used as the first catalyst. In Experiments 1 and 2, care was also taken to ensure that about 90 to 95% of the conversion of the C=C and C=O bonds present took place over this catalyst.

In Comparative Experiment B, only the neutral catalyst B is used. This experiment is essentially a repetition of Example 1 of DE 1 643 856. Merely a lower pressure, a lower linear velocity and, in some cases, a higher gaseous hourly space velocity were established.

COMPARATIVE EXPERIMENT A

Hydrogenation of 2-ethylhexenal
Catalyst A: 100% by volume of 9% Cu and 1.4% Cr$_2$O$_3$ on alkaline SiO$_2$

TABLE 2

| | LHSV 1/h | Ratio H$_2$:EH | Reactor inlet °C. | Reactor jacket °C. | Bromine number mg of Br/100 g | H$_2$SO$_4$ color index | n-Heptane % | 2-Ethyl-hexanal % | 2-Ethyl-hexanol % | Dioctyl ether % | Dioctyl ester % |
|---|---|---|---|---|---|---|---|---|---|---|---|
| a | 0.15 | 39:1 | 135 | 160 | 0.1–0.3 | 300 | — | 0.2 | 95.1 | — | 0.1–0.2 |
| b | 0.20 | 30:1 | 135 | 160 | 0.2–0.4 | >1000 | — | 0.3 | 95.0 | — | 0.2–0.5 |
| c | 0.25 | 24:1 | 135 | 165 | 0.3–0.7 | >1000 | 0.02 | 0.3–0.4 | 94.8 | — | 0.3–0.8 |
| d | 0.30 | 20:1 | 140 | 165 | 0.5–1.0 | >1000 | 0.02 | 0.3–0.4 | 93.7 | 0.02 | 0.7–2.1 |

LHSV = Liquid hourly space velocity of the gasified product (m$^3$ of liquid aldehyde per m$^3$ of catalyst per hour)
EH = 2-Ethylhexenal As shown in table 2, the sulfuric acid color indices are higher, also at higher space velocity, the ester contents are very high.

COMPARATIVE EXPERIMENT B

Hydrogenation of 2-ethylhexenal
Catalyst B: 100% by volume of 10.4% Cu, 4.6% Ni; and 1.4% Cr$_2$O$_3$ on neutral SiO$_2$.

TABLE 3

| | LHSV 1/h | Ratio H$_2$:EH | Reactor inlet °C. | Reactor jacket °C. | Bromine number mg of Br/100 g | H$_2$SO$_4$ color index | n-Heptane % | 2-Ethyl-hexanal % | 2-Ethyl-hexanol % | Dioctyl ether % | Dioctyl ester % |
|---|---|---|---|---|---|---|---|---|---|---|---|
| a | 0.15 | 39:1 | 135 | 160 | 0.05 | 150 | 0.1–0.2 | 0.2 | 95.1 | 0.03 | <0.1 |
| b | 0.20 | 30:1 | 135 | 160 | 0.07 | 150–250 | 0.2–0.4 | 0.3 | 95.0 | 0.08 | 0.1 |
| c | 0.25 | 24:1 | 135 | 160 | 0.1–0.2 | 150–300 | 0.3–0.6 | 0.3–0.4 | 94.8 | 0.07 | 0.1 |
| d | 0.30 | 20:1 | 140 | 165 | 0.1–1.3 | >300 | 1.0–2.0 | 0.3–0.5 | 93.5 | 0.1 | 0.1–0.3 |
| e | 0.35 | 17:1 | 140 | 165 | 0.2–0.5 | >300 | >2.5 | 0.7 | <93 | 0.1–0.3 | 0.1–0.3 |

As shown in table 3, the formation of n-heptane is very high above an LHSV of 0.2 h$^{-1}$.

EXPERIMENT 1

Hydrogenation of 2-ethylhexenal
Catalyst combination A and C: 60% by volume of 9% Cu and 1.4% Cr$_2$O$_3$ on alkaline SiO$_2$ in stage 1 and 40% by volume of 10.5%, Cu, 4.5% Ni: and 1.5% Cr$_2$O$_3$ on acidic SiO$_2$ in stage 2.

TABLE 4

| | LHSV 1/h | Ratio H$_2$:EH | Reactor inlet °C. | Reactor jacket °C. | Bromine number mg of Br/100 g | H$_2$SO$_4$ color index | n-Heptane % | 2-Ethyl-hexanal % | 2-Ethyl-hexanol % | Dioctyl ether % | Dioctyl ester % |
|---|---|---|---|---|---|---|---|---|---|---|---|
| a | 0.15 | 39:1 | 135 | 160 | 0.01 | 50 | 0.02 | 0.2 | ≧96 | ≦0.03 | <0.1 |
| b | 0.20 | 30:1 | 135 | 160 | 0.02 | 50–100 | 0.05 | 0.3 | 95.7 | ≦0.03 | <0.1 |
| c | 0.25 | 24:1 | 135 | 160 | 0.02–0.4 | 100–200 | 0.05–0.10 | 0.3 | 95.6 | ≦0.03 | 0.1 |
| d | 0.30 | 20:1 | 140 | 165 | 0.03–0.10 | 100–200 | 0.05–0.10 | 0.4 | 95.3 | ≦0.03 | 0.2 |
| e | 0.35 | 17:1 | 140 | 165 | 0.1 | 150–300 | 0.05–0.15 | 0.5 | 95.3 | ≦0.03 | 0.2 |
| f | 0.40 | 15:1 | 140 | 165 | 0.1–0.2 | 200–300 | 0.1–0.2 | 0.5 | 96.0 | ≦0.03 | 0.3 |

In Experiment f of Table 4, at a space velocity of 0.4 h$^{-1}$, 1–2% of residue are removed from the evaporator during vaporization.

EXPERIMENT 2

Hydrogenation of 2-ethylhexenal

Catalyst combination A, C and D: 60% by volume of 9% Cu and 1.4% Cr$_2$O$_3$ on alkaline SiO$_2$ in Stage 1, 30% by volume of 10.5% Cu, 4.5% Ni: and 1.5% Cr$_2$O$_3$ on acidic SiO$_2$ in stage 2 and 10% by volume of 0.66% Pd on acidic Al$_2$O$_3$ in stage 3

TABLE 5

| | LHSV 1/h | Ratio H$_2$:EH | Reactor inlet °C. | Reactor jacket °C. | Bromine number mg of Br/100 g | H$_2$SO$_4$ color index | n-Heptane % | 2-Ethyl-hexanal % | 2-Ethyl-hexanol % | Dioctyl ether % | Dioctyl ester % |
|---|---|---|---|---|---|---|---|---|---|---|---|
| a | 0.15 | 39:1 | 135 | 160 | 0.008 | 50 | 0.02 | 0.2 | 96.2 | ≦0.03 | <0.1 |
| b | 0.20 | 30:1 | 135 | 160 | 0.01 | 50 | 0.05 | 0.2 | 95.9 | ≦0.03 | <0.1 |
| c | 0.25 | 24:1 | 135 | 160 | 0.01–00.2 | 50–150 | 0.10 | 0.2 | 95.8 | ≦0.03 | 0.1 |
| d | 0.30 | 20:1 | 140 | 160 | 0.02–0.05 | 100–200 | 0.05–0.10 | 0.2 | 95.4 | ≦0.03 | 0.2 |
| e | 0.35 | 17:1 | 140 | 160 | 0.05–0.15 | 100–250 | 0.05–0.20 | 0.3 | 95.4 | ≦0.03 | 0.2 |
| f | 0.40 | 15:1 | 140 | 160 | 0.02–0.10 | 100–200 | 0.1–0.2 | 0.2 | 96.2 | ≦0.03 | 0.3 |

In Experiment f of Table 5, at a space velocity of 0.4 h$^{-1}$, 1–2% of residue are removed from the evaporator during vaporization.

Experiments 1 and 2 clearly show the improvement in selectivity, color index and bromine number as compared with Comparative Experiments A and B.

Experiment 2 took place under changing conditions, generally at the highest space velocity, for a total of more than 500 days.

EXPERIMENT 3

Hydrogenation of n-butyraldehyde (n-BA)

Catalyst combination A, C and D: 60% by volume of 9% Cu and 1.4% Cr$_2$O$_3$ on alkaline SiO$_2$ in Stage 1, 30% by volume of 10.5% Cu, 4.5% Ni and 1.5% Cr$_2$O$_3$ on acidic SiO$_2$ in stage 2 and 10% by volume of 0.66% pd on acidic Al$_2$O$_3$ in stage 3

TABLE 6

| | LHSV 1/h | Ratio H$_2$:n-BA | Reactor inlet °C. | Reactor jacket °C. | n-Butyr-aldehyde % | n-butanol % | Dibutyl ether % | Butyl butyrate % |
|---|---|---|---|---|---|---|---|---|
| a | 0.30 | 12:1 | 130 | 160 | 0.1 | 99.5 | 0.01 | 0.05 |
| b | 0.40 | 9:1 | 130 | 160 | 0.2 | 99.5 | 0.03 | 0.1 |
| c | 0.50 | 7:1 | 130 | 160 | 0.2 | 99.4 | 0.04 | 0.2 |
| d | 0.60 | 6:1 | 130 | 150 | 0.3 | 99.2 | 0.06 | 0.3 |

EXPERIMENT 4

Hydrogenation of iso-butyraldehyde (iso-BA)

Catalyst combination A, C and D: 60% by volume of 9% Cu and 1.4% Cr$_2$O$_3$ on alkaline SiO$_2$ in Stage 1, 30% by volume of 10.5% Cu, 4.5% Ni and 1.5% Cr$_2$O$_3$ on acidic SiO$_2$ in Stage 2 and 10% by volume of 0.66% Pd on acidic Al$_2$O$_3$ in Stage 3

TABLE 7

| | LHSV 1/h | Ratio H$_2$-iso-BA | Reactor inlet °C. | Reactor jecket °C. | iso-Butyr-aldehyde % | iso-butanol % | Diisobutyl ether % | iso-Butyl isobutyl-rate |
|---|---|---|---|---|---|---|---|---|
| a | 0.30 | 12:1 | 130 | 160 | 0.1 | 99.7 | ≦0.05 | <0.02 |
| b | 0.40 | 9:1 | 130 | 160 | 0.1 | 99.7 | ≦0.05 | <0.02 |
| c | 0.50 | 7:1 | 130 | 160 | 0.1 | 99.7 | ≦0.05 | 0.05 |
| d | 0.60 | 6:1 | 130 | 160 | 0.2 | 99.5 | 0.1 | 0.1 |

Experiments 3 and 4 were carried out during brief interruptions in Experiment 2.

Tables 4 to 7 show that the hydrogenation of saturated and unsaturated aldehydes can be carried out in the sam reactor over the same catalysts according to the invention, with a very good result.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for the preparing saturated alcohol from aldehyde by hydrogenating in the gas phase in several stages comprising:
   a) vaporizing an aldehyde and mixing with hydrogen to form an aldehyde-hydrogen mixture;
   b) hydrogenating said aldehyde-hydrogen mixture with a particulate alkaline copper catalyst in a first reaction stage such that at least 85% of the hydrogenation reactions are carried out; and
   c) hydrogenating said mixture with a particulate nickel containing catalyst in a second reaction stage wherein the carrier material of said particulate nickel-containing catalyst has particle sizes of 1–10 mm and contains 0.05 to 0.5 mmol/g of acidic centers of the surface wherein said acidic centers have an acidic strength H$_o$ of 2.8–4.8.

2. The process according to claim 1, wherein 90 to 98% of the hydrogenation reactions are carried out in the first stage.

3. The process according to claim 1, wherein the carrier material of the catalyst of the second stage has 0.1 to 0.4 mmol/g of acidic centers.

4. The process according to claim 1, wherein the carrier material of the catalyst of the second stage is selected from the group consisting of oxides of silicon and aluminum or a mixture thereof and has a specific surface area of 100 to 600 m$^2$/g.

5. The process according to claim 1, wherein the hydrogenation in the second stage is carried out over a nickel catalyst.

6. The process according to claim 1, wherein the hydrogenation in the second stage is carried out over a nickel/copper catalyst.

7. The process according to claim 6, wherein the weight ratio of copper to nickel is in the range from 5:1 to 1:5.

8. The process according to claims 5, 6 or 7, wherein catalysts impregnated in the edge zone are used.

9. The process according to claim 1, wherein the volume of the catalyst of the second stage accounts for 20 to 70% of the total catalyst volume.

10. The process according to claim 9, wherein the volume is 25 to 45% of the total catalyst volume.

11. The process according to claim 1, further comprising hydrogenating said mixture with a particulate palladium catalyst in a third stage.

12. The process according to claim 11, wherein the volume of the palladium catalyst accounts for 5 to 20% of the total catalyst volume.

13. The process according to claim 11, wherein a palladium catalyst impregnated in the edge zone is used.

14. The process according to claim 1, wherein the inlet temperature of the first stage is 125° to 160° C. and hydrogen and aldehyde are used in a volume ratio of 100:1 to 3:1.

15. The process according to claim 1, wherein hydrogen and aldehyde are used in a volume ratio of 30:1-5:1.

16. The process according to claim 11, wherein the particulate palladium catalyst contains 0.05-5% of palladium.

* * * * *